US011129516B2

(12) United States Patent
Wilson (10) Patent No.: US 11,129,516 B2
(45) Date of Patent: Sep. 28, 2021

(54) POWER SOURCE CONTROL FOR MEDICAL CAPSULES

(71) Applicant: CapsoVision, Inc., Saratoga, CA (US)

(72) Inventor: Gordon C. Wilson, San Francisco, CA (US)

(73) Assignee: CAPSOVISION INC., Saratoga, CA (US)

( * ) Notice: Subject to any disclaimer, the term of this patent is extended or adjusted under 35 U.S.C. 154(b) by 532 days.

(21) Appl. No.: 16/179,873

(22) Filed: Nov. 2, 2018

(65) Prior Publication Data

US 2019/0069758 A1 Mar. 7, 2019

Related U.S. Application Data

(62) Division of application No. 14/272,210, filed as application No. PCT/US2013/023034 on Jan. 24, 2013, now Pat. No. 10,206,557.

(Continued)

(51) Int. Cl.
*A61B 1/00* (2006.01)
*A61B 1/04* (2006.01)
(Continued)

(52) U.S. Cl.
CPC ...... *A61B 1/00032* (2013.01); *A61B 1/00025* (2013.01); *A61B 1/00036* (2013.01); *A61B 1/041* (2013.01); *H01M 6/5072* (2013.01); *A61B 1/0002* (2013.01); *A61B 1/00027* (2013.01); *A61B 1/00034* (2013.01); *A61B 1/00039* (2013.01); *A61B 1/00177* (2013.01); *A61B 1/0615* (2013.01)

(58) Field of Classification Search
CPC . A61B 1/00032; A61B 1/00036; A61B 1/041; A61B 1/0002; A61B 1/00025; A61B 1/00027; A61B 1/00034; H01M 6/5072
See application file for complete search history.

(56) References Cited

U.S. PATENT DOCUMENTS 10,869,594 B2 * 12/2020 Wilson ............... A61B 1/00013
2003/0171648 A1 * 9/2003 Yokoi .................... A61B 1/041
600/109

(Continued)

*Primary Examiner* — Timothy J Neal
*Assistant Examiner* — William B Chou
(74) *Attorney, Agent, or Firm* — Blairtech Solution LLC (57) ABSTRACT

A power source apparatus and a system incorporating said power source for medical capsules are disclosed. A medical capsule often includes a power source sealed in a housing. Embodiments of the present invention allow the medical capsule to enable/disable electrical power supplied to a sub-system in the capsule device without special tools and/or skills after the medical capsule is manufactured. In one embodiment, the power source apparatus comprises a plunger responsive to a magnetic field, a spring to interact with the plunger, a battery and a control piece. The plunger is moved between first and second positions according to a magnetic field applied externally. Accordingly, the control piece enables or disables the power depending on the plunger positions. In another embodiment, a capsule system uses an electrical interconnect with pressure contacts between the power source and the capsule sub-system connecting the second circuit board to the power-output nodes.

18 Claims, 11 Drawing Sheets

Related U.S. Application Data (60) Provisional application No. 61/603,028, filed on Feb. 24, 2012.

(51) Int. Cl.
*A61B 1/06* (2006.01)
*H01M 6/50* (2006.01)

(56) References Cited

U.S. PATENT DOCUMENTS

| | | | |
|---|---|---|---|
| 2005/0075559 A1 | 4/2005 | Houzego et al. | |
| 2006/0264704 A1* | 11/2006 | Fujimori | A61B 1/041 600/101 |
| 2007/0229656 A1* | 10/2007 | Khait | H01M 50/213 348/77 |
| 2008/0167523 A1* | 7/2008 | Uchiyama | A61B 5/073 600/114 |
| 2010/0016667 A1* | 1/2010 | Segawa | A61B 1/0011 600/118 |
| 2010/0049012 A1 | 2/2010 | Dijksman et al. | |
| 2010/0076258 A1* | 3/2010 | Segawa | A61B 1/042 600/101 |
| 2010/0130822 A1 | 5/2010 | Katayama et al. | |
| 2010/0286791 A1* | 11/2010 | Goldsmith | A61B 17/0057 623/23.7 |
| 2012/0238811 A1* | 9/2012 | Tanaka | A61B 1/00144 600/109 |
| 2020/0251808 A1* | 8/2020 | Nishi | H01Q 1/273 |
| 2021/0085163 A1* | 3/2021 | Chen | A61B 1/00032 |

* cited by examiner

POWER SOURCE CONTROL FOR MEDICAL CAPSULES

CROSS REFERENCE

The present invention is a divisional application of and claims priority to U.S. Non-Provisional application, Ser. No. 14/372,210, filed on Jul. 14, 2014, which corresponds to U.S. National Stage filing of PCT/US2013/023034, filed on Jan. 24, 2013. The PCT/US2013/023034 application claims priority to U.S. Provisional Patent Application, No. 61/603,028, filed on Feb. 24, 2012. The U.S. Patent Application, PCT application and U.S. Provisional Patent Application are hereby incorporated by reference in their entireties.

FIELD OF THE INVENTION

The present invention relates to in vivo medical devices that are administered into the human body. In particular, the present invention relates to power source control for medical capsules.

BACKGROUND AND RELATED ART

Various types of medical capsules have been widely used in the field, where the medical capsules are ingested into a human body for in vivo monitoring or examining purposes. For example, a medical capsule can be used to monitor the pH value of the gastrointestinal tract or temperature of different human organs. A medical capsule may also be used to deliver medicines to desired spots inside the human body or to collect samples, such as body fluids, inside a human body. Usually, the medical capsule includes a power source, such as batteries, so that the capsule can monitor/measure data, dispense medicine, or collect samples inside the human body without the need of external power. The power source along and other components of the medical capsule are enclosed inside a smooth housing adapted for easy swallowing. The power source and other components of the medical capsule are sealed in a housing. It is not easy to access the power source and other components of the medical capsule, after the medical capsule is manufactured, to enable or disable the power without special tools and/or skills. Furthermore, the medical capsule may not be administered soon after it is manufactured. Also, the medical capsule may have to be operational for extended hours during the course of travelling through the human tract; the power source is preferred to be disabled until right before it is administered into the human body. In other words, the power source to the medical capsule is enabled when the capsule is ready for administering into a patient's body. It is desirable to develop power-efficient, reliable and compact apparatus of power source control for medical capsules. The housing for the medical capsule may be fully sealed or watertight so that there is no direct access to any components inside the housing. Therefore, the power source has to be operated without opening the housing.

BRIEF SUMMARY OF THE INVENTION

A power source apparatus for medical capsule is disclosed. In one embodiment according to the present invention, the power source apparatus for medical capsules comprises a plunger, a spring, a battery and a circuit piece. The plunger is responsive to a magnetic field. The plunger is pushed by the spring to a first position when the magnetic field is removed, and the plunger compresses the spring to a second position when the magnetic field is applied. The circuit piece comprises power output contacts, and wherein power from the battery is enabled at the power output contacts with the plunger at the first position and the power from the battery is disabled at the power output contacts with the plunger at the second position. In one embodiment according to the present invention, the spring is disposed to have one end of the spring against a fixed structure and other end of the spring against a top side of the plunger. In another embodiment according to the present invention, the plunger comprises a rod-portion and a flange-portion at a lower end of the rod-portion, and wherein the spring is disposed around the rod-portion of the plunger to have one end of the spring against a fixed structure and other end of the spring against the flange. In one embodiment, the circuit piece comprises a circuit board attached to the plunger. When the plunger is moved between the first position and the second position, it causes the circuit board connected to or disconnected from a terminal of the battery and consequently causes the power source enabled or disabled respectively. In another embodiment according to the invention, the plunger comprises two conductive bumps to cause the battery enabled or disabled depending on the plunge at the first position or the second position. The circuit piece comprises a circuit board having a battery-contact-pad on one side of the circuit board and power-control-pads on other side of the circuit board, wherein the circuit board is disposed in a stationary position to make electrical contact between the battery-contact-pad and a terminal of the battery, and wherein said two power-control-pads are electrically connected by said two conductive bumps when the plunger is at the first position and electrically disconnected when the plunger is at the second position.

A capsule camera system including the power source is also disclosed. In one embodiment according to the present invention, the capsule camera system comprises a housing adapted to be swallowed, a power source within the housing, and a capsule sub-system within the housing, wherein the capsule sub-system is coupled to the power output contacts to receive power from the power source. The power source within the housing comprises a plunger responsive to a magnetic field, a spring disposed to interact with the plunger, a battery, and a circuit piece coupled to the battery and the plunger. The plunger is pushed by the spring to a first position when the magnetic field is removed, and the plunger compresses the spring to a second position when the magnetic field is applied. The circuit piece comprises power output contacts, and wherein power from the battery is enabled at the power output contacts with the plunger at the first position and the power from the battery is disabled at the power output contacts with the plunger at the second position. The capsule sub-system within the housing comprises a light source, a camera for capturing a digital image of a scene illuminated by the light source, and an archival memory to store or a transmitter to wirelessly transmit data corresponding to the digital image and other data.

DETAILED DESCRIPTION OF THE INVENTION

Various types of medical capsules have been widely used in the field, where the medical capsules are ingested into a human body for in vivo monitoring or examining purposes. For example, a medical capsule can be used to monitor the pH value of the gastrointestinal tract or temperature of different human organs. A medical capsule may also be used to deliver medicines to desired spots inside the human body or to collect samples, such as body fluids, inside a human body. Usually, the medical capsule includes a power source, such as batteries, so that the capsule can monitor/measure data, dispense medicine, or collect samples inside the human body without the need of external power. The power source along and other components of the medical capsule are enclosed inside a smooth housing adapted for easy swallowing. The power source and other components of the medical capsule are sealed in a housing. It is not easy to access the power source and other components of the medical capsule, after the medical capsule is manufactured, to enable or disable the power without special tools and/or skills. Furthermore, the medical capsule may not be administered soon after it is manufactured. Also, the medical capsule may have to be operational for extended hours during the course of travelling through the human tract; the power source is preferred to be disabled until right before it is administered into the human body. In other words, the power source to the medical capsule is enabled when the capsule is ready for administering into a patient's body. It is desirable to develop power-efficient, reliable and compact apparatus of power source control for medical capsules. The housing for the medical capsule may be fully sealed or watertight so that there is no direct access to any components inside the housing. Therefore, the power source has to be operated without opening the housing.

Capsule camera is a type of medical capsule that has been widely used in the medical field as an alternative to the conventional endoscopy to examine the gastrointestinal tract. The camera is housed in a swallowable capsule, along with a radio transmitter for transmitting data, primarily comprising images recorded by the digital camera, to an external receiver/data recorder or an on-board storage to store the captured images. The capsule may also include a radio receiver for receiving instructions or other data from a base-station transmitter. The capsule travels through the gastrointestinal tract and will be evacuated from the human body after long hours. The speed of the capsule movement inside the body varies greatly from person to person. Also the speed varies greatly for different parts of the GI tract. For example, the average transit time for a capsule camera to travel through the small bowel is about 5 hours while the average transit time to travel through the colon is about 10 hours. Therefore, power becomes even more critical for the success of capsule camera, and a power efficient and easy to use power control is very desirable.

In the following description, various aspects of the present invention will be described. For purposes of illustration, specific configurations and details are set forth in order to provide a thorough understanding of the present invention. However, it will also be apparent to those skilled in the art that the present invention may be practiced without the specific details presented herein. Furthermore, well-known features may be omitted or simplified in order not to obscure the present invention.

Figure 1A:
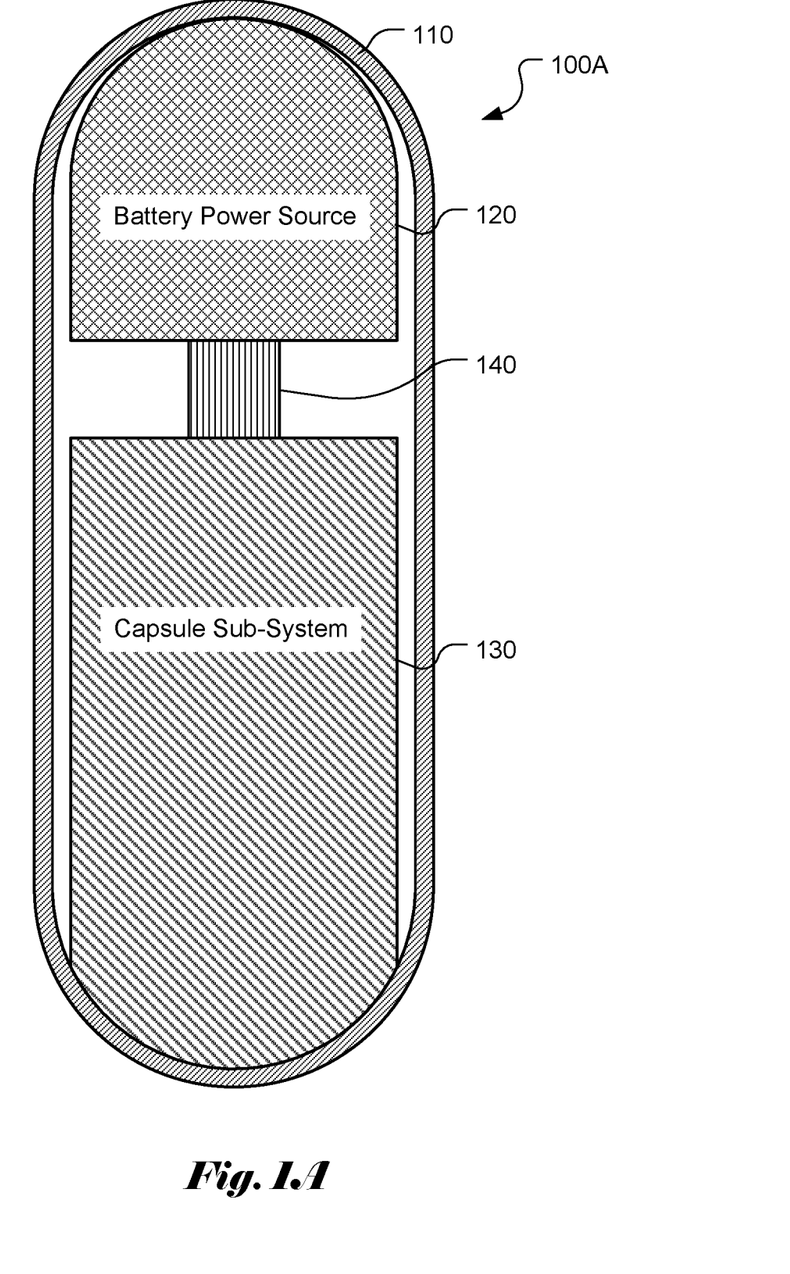
FIG. 1A illustrates one example of the capsule camera system comprising a battery power source and a capsule sub-system interconnected using a cable.

FIG. 1A shows a swallowable capsule system 100A comprising battery power source 120 and capsule sub-system 130. Battery power source 120 and capsule sub-system 130 are interconnected by electrical interconnection 140. Battery power source 120, capsule sub-system 130, and electrical interconnection 140 are enclosed inside housing 110. Capsule sub-system 130 may include processor, memory, image sensor, illumination source, on-board archival memory, and output port. Instead of using on-board storage, the capsule camera may also use a transmitter with antenna to transmit the captured images to a base station located outside the human body. The capsule may use a wireless transmitter that sends signals through the body by electrical conduction. Furthermore, the capsule camera may also include other sensors such as pH or temperature sensor. Battery power source 120 includes control mechanism so that the power can be enabled or disabled by applying a control means externally.

Figure 1B:
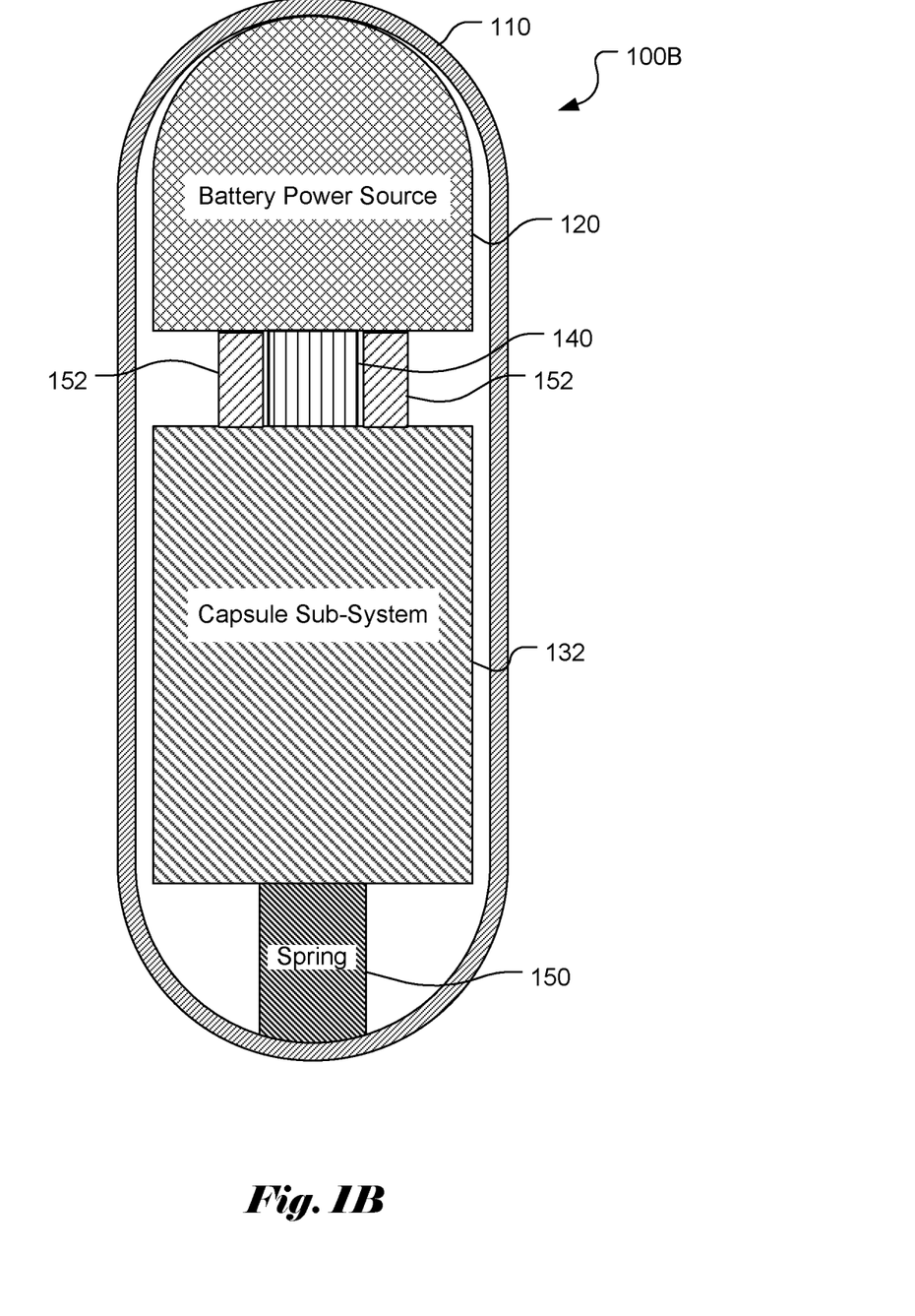
FIG. 1B illustrates one example of the capsule camera system comprising a battery power source and a capsule sub-system, where a spring is used to keep parts snug fit inside the housing.

FIG. 1B illustrates an alternative capsule camera arrangement 100B inside the capsule camera, where spring 150 is used to keep the parts snug fit inside the housing. Capsule sub-system 132 is pushed by spring 150 toward battery power source 120. A stop mechanism 152 may be disposed between the battery power source and the capsule subsystem to limit how far the spring pushes the capsule subsystem towards battery power supply. The stop mechanism 152 may be an extruded structure from the housing or a rigid spacer between capsule sub-system 132 and battery power source 120. Other means of stop mechanism may also be used. Electrical interconnection 140 may be implemented using flexible cable or rigid connector. The flexible cable may include multiple insulated flexible conductors (wires) inside or on a rubber matrix to provide a compliant electrical interconnect. The wires may be metallic wires or consist of carbon particles embedded in layers of the rubber matrix. The flexible cable may consist of a rubber block matrix with flexible conductive stripes wrapping around the side of the block from top to bottom, which may be made of silver, gold, or other conductive material, coating the outside of the rubber block. For example, Fujiply of Japan makes various flexible interconnects of these types under the name "zebra connector". The flexible cable makes a pressure contact to the pads on the PCB. The conductors of the cable are not bonded to the pads by solder, welding, or conductive adhesive. Rather the contact is made by the two conductors touching the pad with some pressure. The pressure is produced by the force exerted by spring 150 (as shown in FIG. 1B) or by the spring force of the compressed cable itself.

Figure 1C:
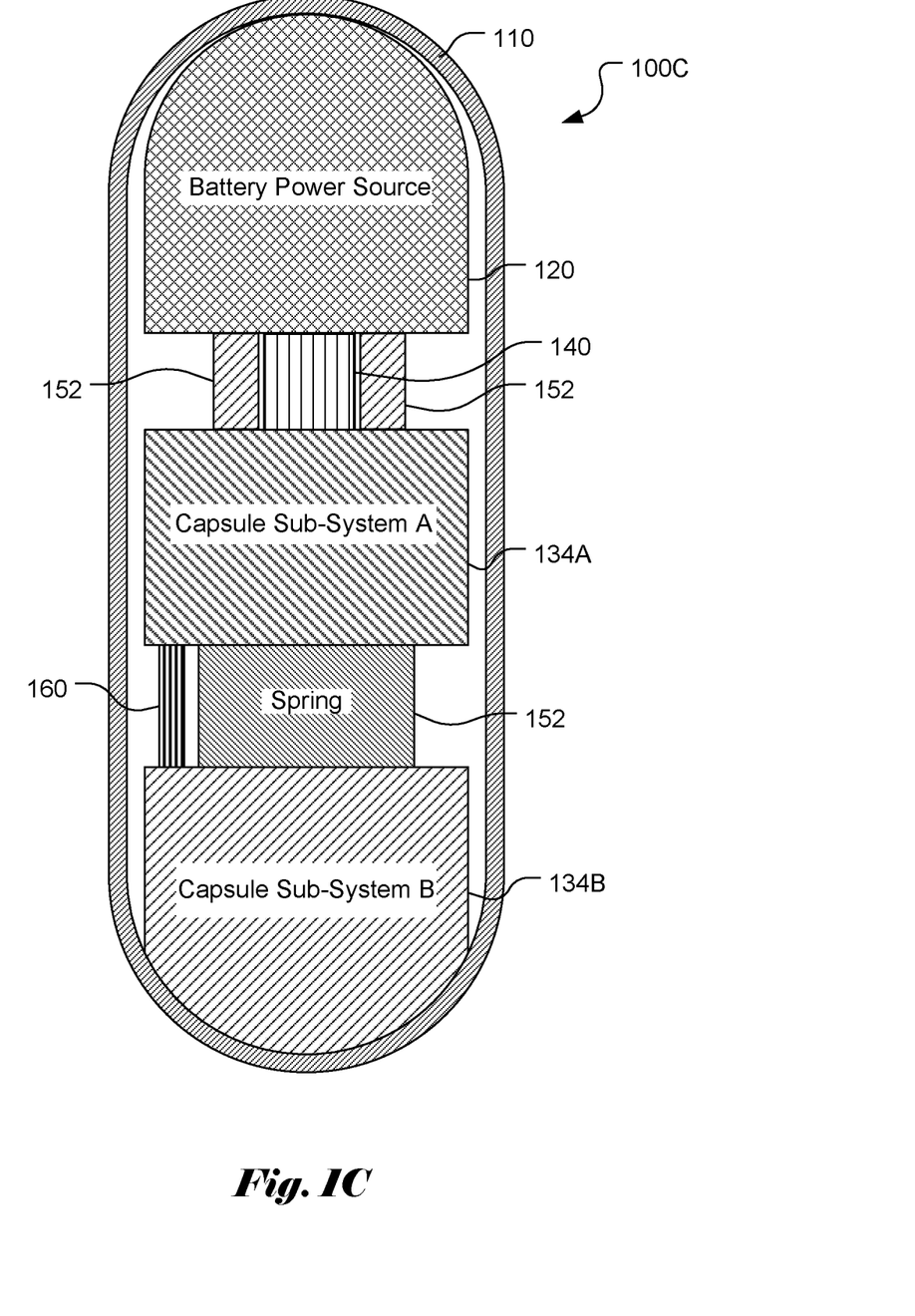
FIG. 1C illustrates one example of the capsule camera system comprising a battery power source and two capsule sub-systems, where a spring is used to keep parts snug fit inside the housing.

When a rigid connector is used, the rigid connector may also serve as the spacer to provide the stop mechanism. FIG. 1C illustrates another alternative capsule camera arrangement 100C inside the capsule camera, where the capsule camera comprises capsule sub-system A (134A) and capsule sub-system B (134B) interconnected by electrical interconnect 160. Spring 152 is used to keep the parts snug fit inside the housing. Spring 152 pushes capsule sub-system A (134A) toward battery power source 120 and there is a need for a mechanism to stop capsule sub-system 134A from moving beyond a point. Spring 152 also pushes capsule sub-system B (134B) against the bottom end of housing 110 to keep components inside the housing snug fit. This implies that components will not move relative to each when the capsule is accelerated, up to some level of acceleration. Also, electrical contact is maintained between adjacent components within the battery power source and within the capsule subassembly and between the capsule subassembly, the electrical interconnect, and the battery power source.

Figure 2:
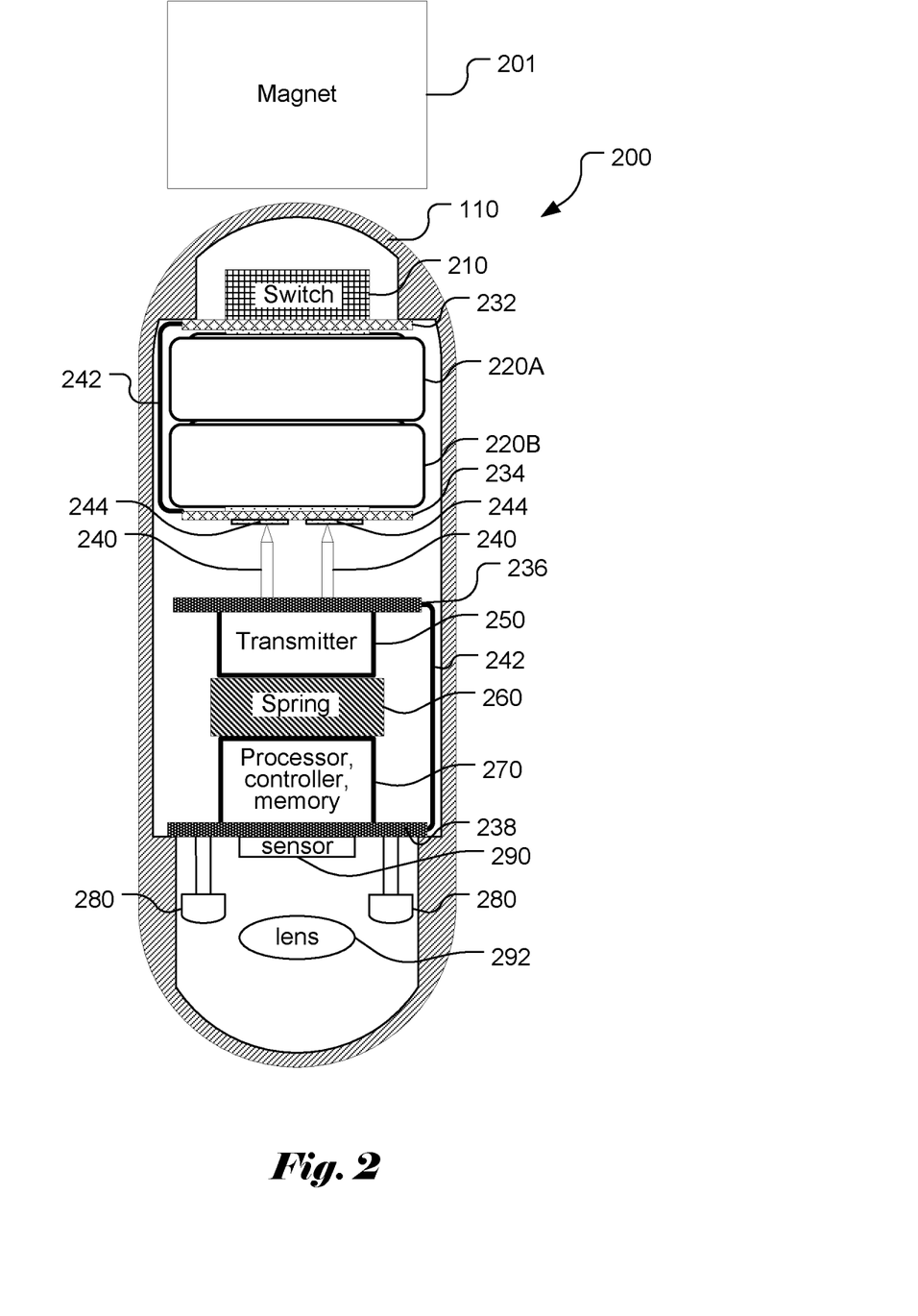
FIG. 2 illustrates one example of the capsule camera system incorporating a battery power source according to one embodiment of the present invention.

FIG. 2 illustrates one embodiment according to the present invention where the battery power source comprises switch 210, battery pack (batteries 220A and 220B), circuit boards or PCB pads 232 and 234, and interconnection cables 242 between circuit boards or PCB pads 232 and 234. While two batteries are used for the battery pack as an example, a single battery or more than two batteries may also be used. A battery typically has two terminal ("+" and "−" terminals). When multiple batteries are used, they can be configured for serial connection or parallel connection. Circuit boards or PCB pads 232 and 234 are mainly used to route power from battery pack to sub-system and may not need any active or passive components. While circuit boards are used as an example to provide connectivity for battery power under the control of an external magnet, other circuit piece may also be used. For example, flat flexible circuit may also be used. The battery power source supplies power to the capsule system through contact nodes 244 on circuit board 234. Circuit boards 232 and 234 may be implemented based on rigid board or flexible board. Switch 210 controls power source enabling and disabling. An electronic switch using a light sensor to control enable/disable will consume power to operate. Therefore a non-power consuming means is a preferred way to implement the switch. As shown in FIG. 2, an external magnet 201 is used with switch 210 for non-power consuming operations. During storage or transport, the power to the capsule system is turned off and the power is supplied to the capsule system shortly before it is administered into the human body. Other components enclosed in housing 110 may include transmitter 250, processor/controller/memory 270, LEDs 280, sensor 290 and lens 292 as shown in FIG. 2. Two or more conductive pins 240 are used to connect power source to the sub-systems. The bases of conductive pins 240 at the lower end can be soldered onto rigid circuit board 236. The tips of conductive pins 240 on the top side are pushed by spring 260 to make pressure contacts with circuit board 234. Pins 240 may be compliant. For example they may be "pogo pins" comprising spring loaded plunger pins sliding in tubular receptacles. If pins 240 are compliant, spring 260 may be omitted. Parts for transmitter 250 are also mounted on circuit board 236. Similarly, processor, controller, memory, sensor, light source (LEDs) and other required circuits are mounted on circuit board 238. Lens 292 projects field of view onto sensor 290. Lens 292 is supported by or attached to a lens holding structure which is not shown in the FIG. 2. Circuit boards 236 and 238 are interconnected by cable 242 to carry power and signals between the two boards. The components shown in FIG. 2 illustrate an example of interconnection within the capsule housing and the drawing may not be shown according to the actual scale. The capsule camera in FIG. 2 shows an example of forward-looking arrangement, where the field of view covers the front side (bottom side) of the capsule camera.

Figure 3:
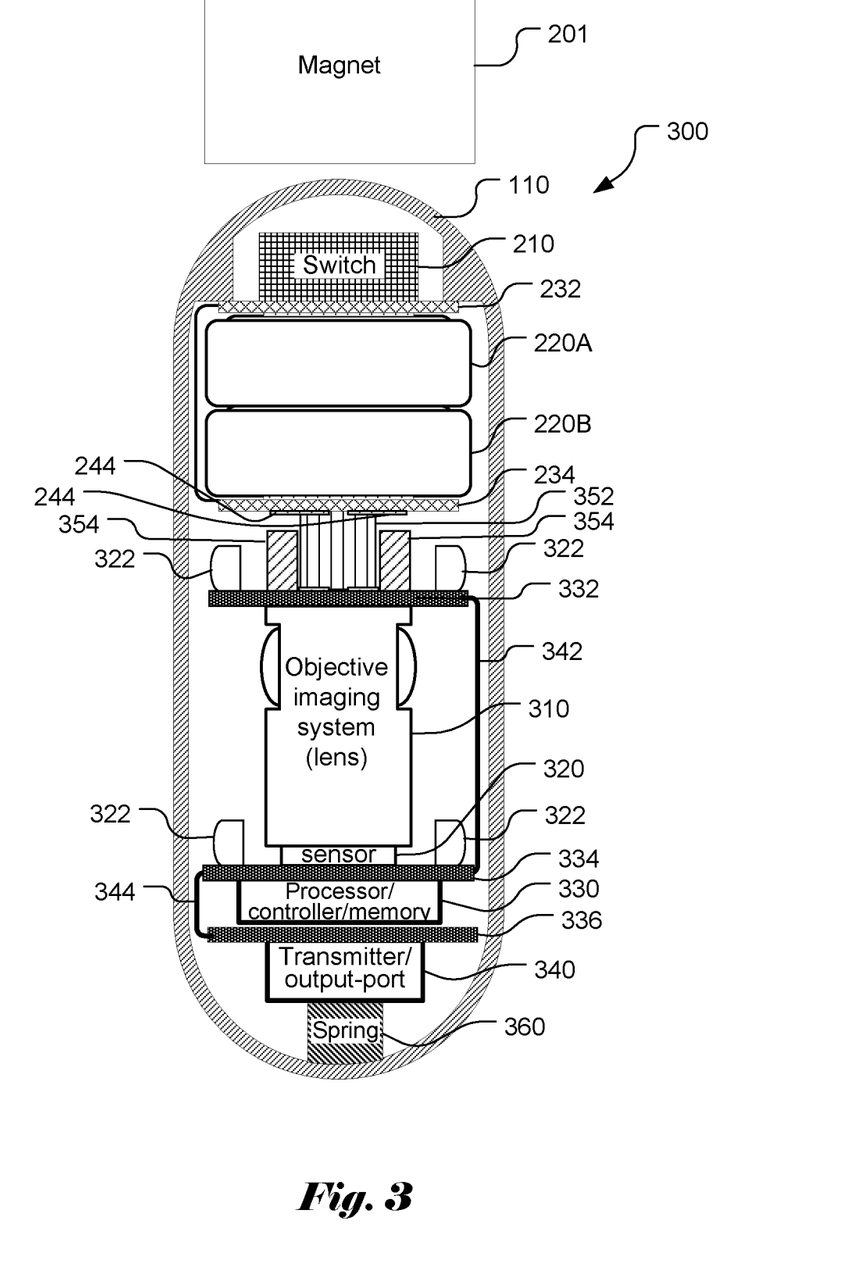
FIG. 3 illustrates one example of the capsule camera system incorporating a battery power source according to another embodiment of the present invention.

FIG. 3 illustrates another embodiment according to the present invention where the capsule camera 300 has a panoramic view around the camera. Capsule camera 300 includes the same battery power source as that for capsule camera 200. The objective imaging system (lens) 310 combines fields of view from two or more sides around the capsule camera and projects the combined fields of view onto sensor 320. Circuit boards 334 and 336 are used to accommodate various components such as sensor 320, processor/controller/memory 330, transmitter/output port 340, light source (LEDs) 322 and other required circuits. Circuit boards 334 and 336 are interconnected by cable 344 to pass power and signals. Circuit board 332 is used to accommodate additional light source (LEDs) 322 and to connect to power source through electrical interconnect 352, which may be made of flexible cable or rigid connectors. In case that electrical interconnect 352 is made of flexible cable, holders 354 may be needed. The holders constrain the lateral position of the flexible cable. The holders may also serve as a stop mechanism, limiting how much electrical interconnect 352 is compressed by the force created by the spring 360.

Figure 4:
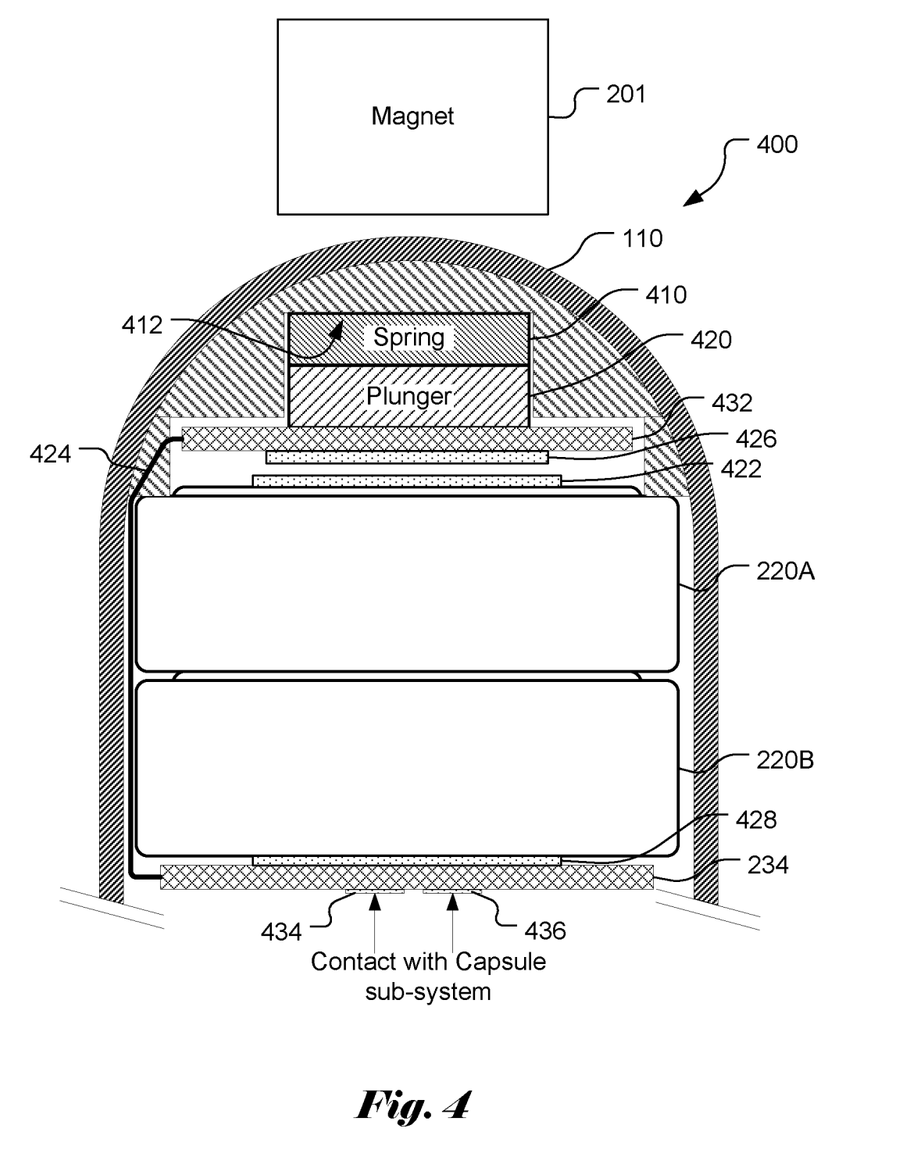
FIG. 4 illustrates one example of the battery power source embodying the present invention, where a circuit board is attached to a plunger for power enable/disable control.

FIG. 4 illustrates an exemplary battery power source 400 embodying the present invention where plunger 420 is shown in a pulled-up position to cause power source disabled. The switch comprises spring 410, plunger 420 and circuit board (or circuit pad) 432. Circuit board 432 is attached to plunger 420 so that circuit board 432 can be pulled up or pushed down by plunger 420. When circuit board 432 is pushed down, circuit board 432 will cause power source enabled. For example, the first polarity terminal on the top side of battery 220A is connected to a node on circuit board 432 when circuit board 432 is pushed down by plunger 420. The first polarity terminal on the top side of battery 220A is then routed to pad 434 on circuit board 234. The second polarity terminal is routed to another pad 436 on circuit board 234 by contacting a pad with the bottom side of battery 220B. The top terminal of 220B contacts the bottom terminal of 220A. Therefore, when circuit board 432 is pushed down by plunger 420, both polarity terminals are routed to contact pads 434 and 436 on circuit board 234 to enable power source. When circuit board 432 is pulled up by plunger 420, one polarity terminal is disconnected from circuit board 234 to disable the power source. Spring 410 is placed on top of plunger 420 and is stopped on the top end by a fixed structure 412. The plunger has two sides with one side toward the spring and the other side toward circuit board 432. The side of the plunger toward the spring is called the top side in this disclosure. Without external force, spring 410 is configured to be compressed so that spring 410 pushes plunger 420 and fixed structure 412, which may be part of the housing 110 or a separate piece. Since fixed structure is stationary, spring 410 will push plunger 420 down to enable power source. However, when the top end of the capsule camera is placed near a magnet or a magnetic field is applied to the top of the capsule camera, the magnetic force will pull plunger 420 up so that the contact pad 426 on the bottom of circuit board 432 will be disconnected from the first polarity terminal on the top of battery 220A. Alternatively, spring 410 may be attached to fixed structure 412 or part of fixed structure 412 to cause plunger 420 to be pressed down without external force. When plunger 420 is pulled up by magnetic force, spring 410 is further compressed. Plunger 420 is made of or contains ferromagnetic materials, such as iron or ferrimagnetic material such as ferrite. An optional conductor between contact pad 422 and battery may be used. FIG. 4 illustrates a scenario that magnet 201 is placed near the top of the capsule camera to cause the switch to disable the power source. Spring 410 may be in various forms or may be made of various materials. For example the spring may be made of a foam material with sufficient elasticity so that it can be compressed when pressure is applied and returns to normal form quickly with the pressure removed. The spring may also be a coil spring or a cantilever spring. Spring 410 in one embodiment according to the present invention can be in a first compressed position when spring 410 is pressed by plunger 420. The action that plunger 420 presses spring 410 is caused by the magnetic force and the action will cause at least one battery terminal disconnected from power output nodes 434 and 436. When the magnetic force is removed, spring 410 tends to recover its original shape and subsequently pushes plunger 420 down to enable the power source. Accordingly, an external magnetic force is used to disable the power source and a mechanical means (spring) is used to enable the power source. Until the capsule device is ready for swallowing, the device is normally off and no internal power is required to keep it off.

Figure 5:
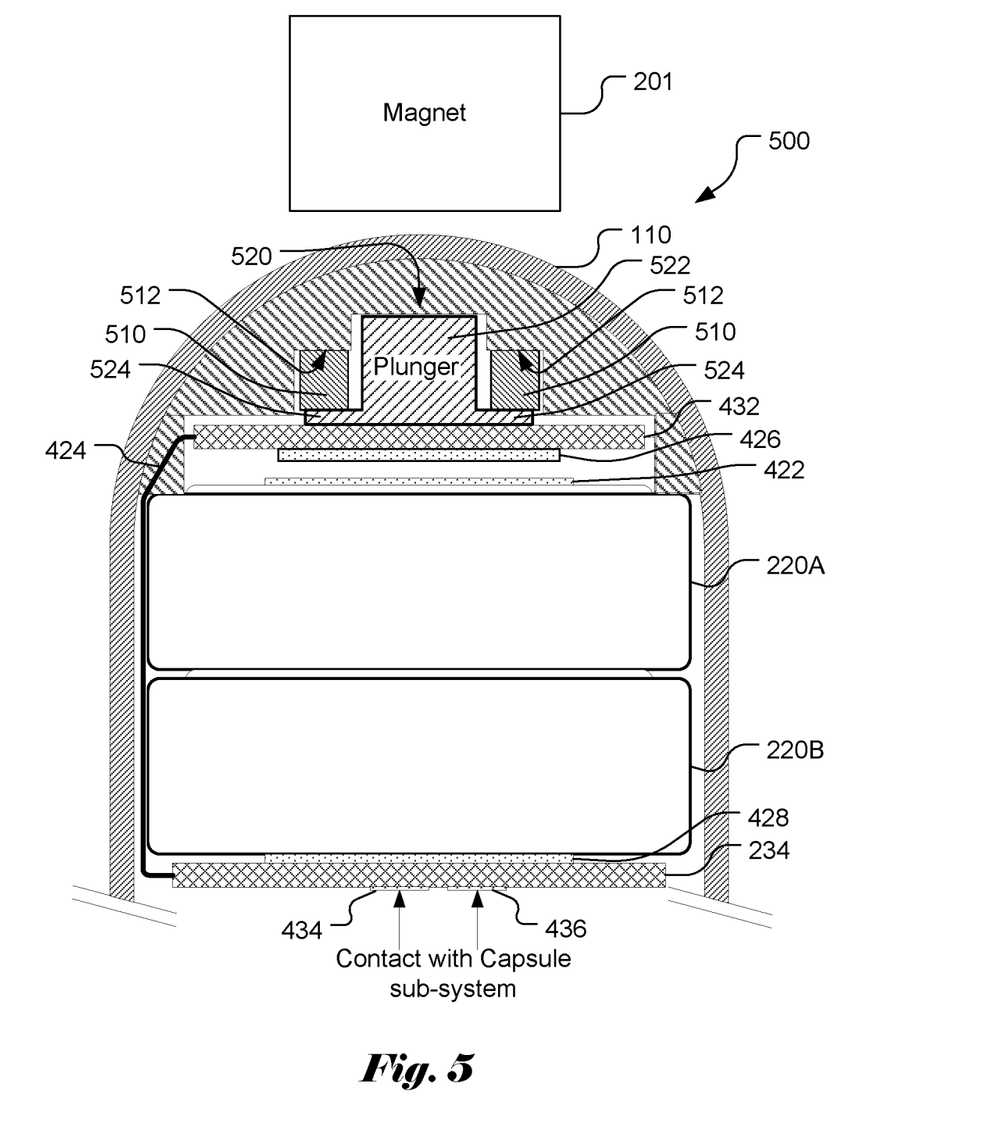
FIG. 5 illustrates another example of the battery power source embodying the present invention, where a circuit board is attached to a plunger for power enable/disable control.

FIG. 5 illustrates an alternative battery power source embodying the present invention, where plunger 520 is shown in a pulled-up position to cause power source disabled. Plunger 520 comprises a rod portion 522 and a flange portion 524. Spring 510 can be a ring-shaped device surrounding plunger 520. Alternatively, spring 510 may be implemented in two separate pieces on two sides of plunger 520. Spring 510 is always in a compressed state so that it pushes against a fixed structure 512 and flange 524 of plunger 520. Fixed structure 512 may be part of housing 110 or a separate piece. In another embodiment according to the present invention, spring 510 may be implemented in multiple separate pieces evenly distributed around plunger 520. Circuit board 432 is attached to plunger 520 so that circuit board 432 is pulled away from the top side of battery 220A when plunger 520 is pulled up by magnetic force. Similar to the configuration of FIG. 4, spring 510 will press flange portion 524 of plunger 510 down to cause pad 426 on circuit board 432 to connect to the top side of battery 220A when the magnetic force is removed. Alternatively, spring 510 may be attached to fixed structure 512 or part of fixed structure 512 to cause plunger 520 to be pressed down without external force.

Figure 6:
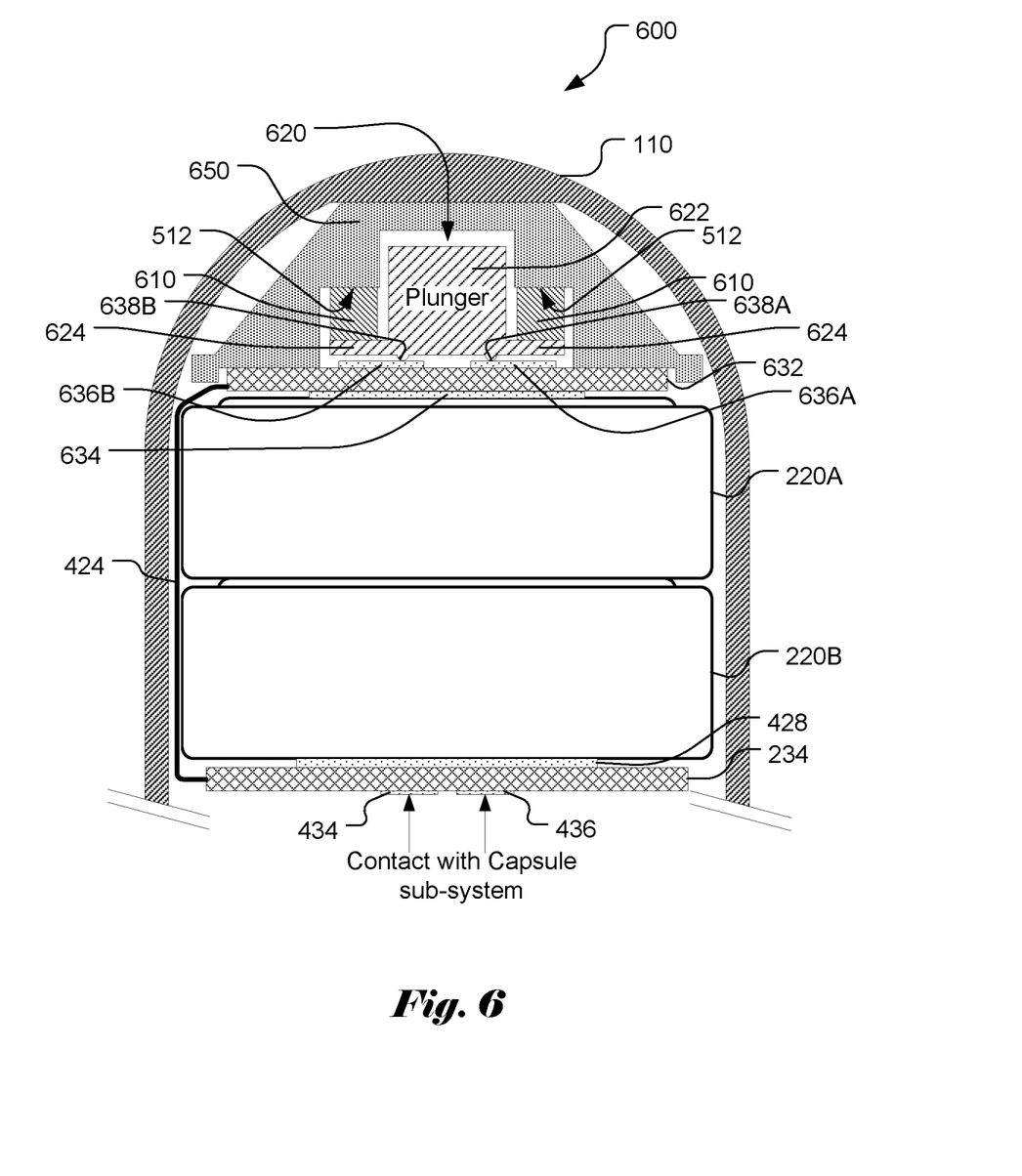
FIG. 6 illustrates one example of the battery power source embodying the present invention, where a plunger with conducting bumps is used for power enable/disable control.

FIG. 6 illustrates another alternative battery power source 600 embodying the present invention, where plunger 620 is shown in a pushed-down position to cause power source enabled. Plunger 620 comprises a rod portion 622 and a flange portion 624. The flange may be located at the lower end of the rod, as shown in FIG. 6, or further up the rod. Spring 610 and plunger 620 are configured in a similar way as that of FIG. 5. However, circuit board 632 is stationary and pad 634 on circuit board 632 is always connected to the top side of battery 220A. There are two pads 636A and 636B on the top side of circuit board 632. One of the two pads is connected to the top side of battery 220A and the other pad is connected to one battery terminal node on circuit board 234 through cable 424. The bottom side of battery 220B is routed to the other battery terminal node on circuit board 234. When power control pads 636A and 636B are electrically connected, the power source is enabled since both battery polarities are routed to the battery terminal pads on the bottom of circuit board 234. Two conductive bumps 638A and 638B on the bottom side of plunger 620 are electrically connected. Alternatively, a single raised ring could replace the two bumps. Alternatively, conductive bumps may be attached to the pads rather than on the plunger. Pointed or edged structures that reduce contact area will increase contact pressure for a given plunger force. Other structures to facilitate electrical connection between 638A and 638B via the plunger known to a skilled person may also be used. When plunger 620 is pressed down by spring 610 on flange 624, conductive bumps 638A and 638B will contact pads 636A and 636B respectively to cause pad 636A electrically connected to pad 636B to enable power source. FIG. 6 also illustrates an exemplary structure, i.e., switch holder 650, to hold various parts of the switch in position. Switch holder 650 is configured to accommodate spring 610, plunger 620 and circuit board 632 and to allow plunger 620 to move up and down. Alternatively, spring 610 may be attached to fixed structure 512 or part of switch holder 650 to cause plunger 620 to be pressed down without external force.

Figure 7:
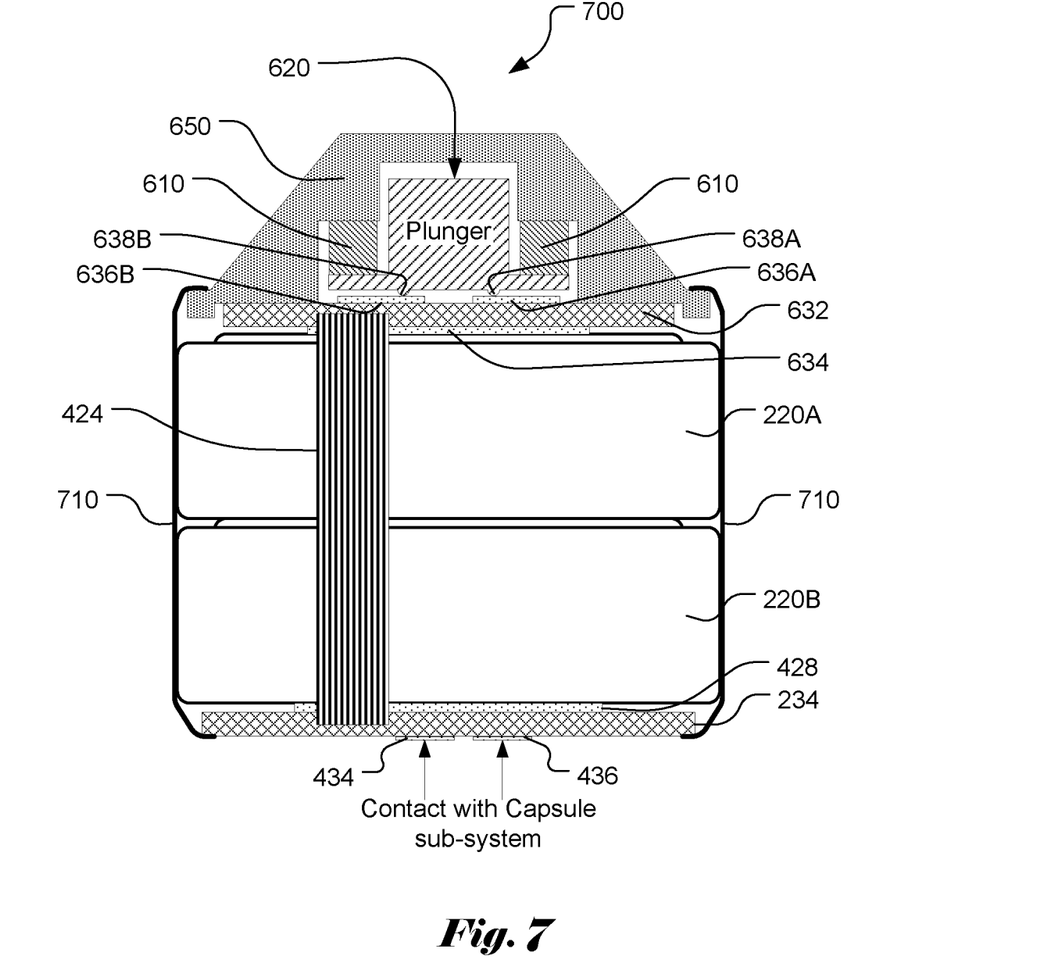
FIG. 7 illustrates one example of the battery power source embodying the present invention, where the battery power source is shrink-wrapped into a module.

FIG. 7 illustrates yet another alternative battery power source 700 embodying the present invention, where plunger 620 is shown in a pushed-down position to cause power source enabled. Battery power source 700 is shown outside capsule housing 110. Battery power source 700 shown in FIG. 7 is in a modular form factor where all parts are held together for easy handling. Another advantage of the modular form factor is to simplify the capsule camera manufacturing. Power source module 700 may be manufactured and tested separately from the rest of the system. When the capsule camera is assembled, power source module 700 can be inserted into housing 110. FIG. 7 illustrates an example of using film material 710 to wrap around the parts for battery power source. In one embodiment according to the present invention, the parts for battery power source are stacked vertically. Film material 710 may be shrink wrapped around the vertically stacked parts, where the vertically stacked parts can be put into film material 710 having a tube shape and heat is applied to cause film material 710 to shrink. After film material 710 shrinks, all the parts for the power source module 700, including switch holder 650, spring 610, plunger 620 circuit boards 632 and 234, cable 424, and batteries 220A and 220B, will be held together tightly by film material 710.

Various embodiments according to the present invention of battery power source for capsule camera have been described above via several examples. The capsule camera incorporating battery power source according to the present invention is capable of enabling power by removing magnetic field applied. During storage or transportation of the capsule camera, magnetic field is applied to keep the power in a disabled state. The magnetic field may be generated from a magnet or using an electrical means.

One or more magnets may be placed at the tip of the capsule or on one or more sides of the capsule to actuate the switch and turn off the capsule.

Figure 8A:
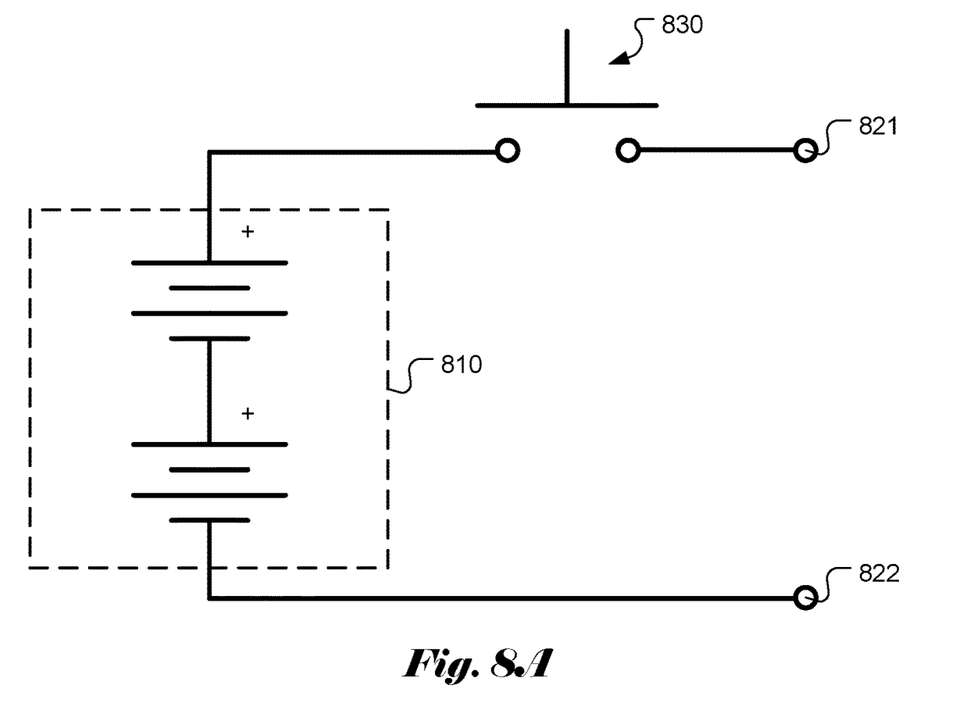
FIGS. 8A-B illustrate two exemplary circuit schematics for the power source with two batteries in series, where a switch incorporating an embodiment of the present invention is connected in series with a power output node and a battery pole.
Figure 8B:
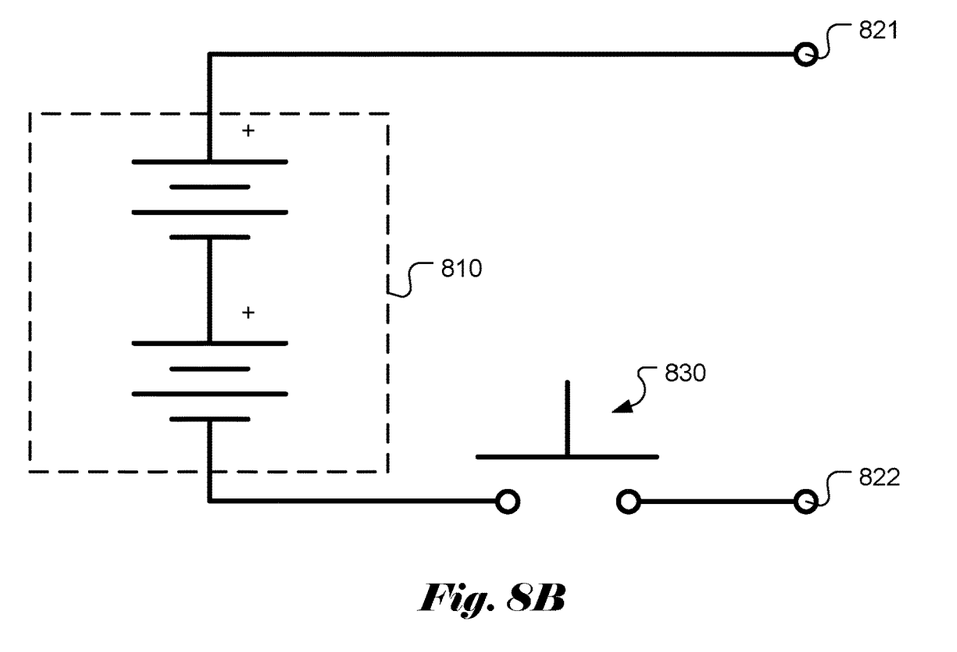

FIG. 8A and FIG. 8B illustrate two exemplary circuit schematics of the power source with two batteries in series. Alternatively, one battery or more than two batteries could be used in series. Also, batteries could be connected in parallel or a combination of parallel and series connections to form a battery assembly. The battery assembly 810 has two polarities, positive and negative. The battery assembly poles are connected to the power source output nodes 821 and 822. A switch 830 may be placed between the battery assembly and one or both of the output power nodes. In FIG. 8A, switch 830 is connected in series between the positive battery pole and the positive output node. In FIG. 8B, switch 830 is placed between the negative battery pole and the negative output node. In some embodiments the switch may be positioned inside a capsules sub-system rather than in the power source.

Figure 9:
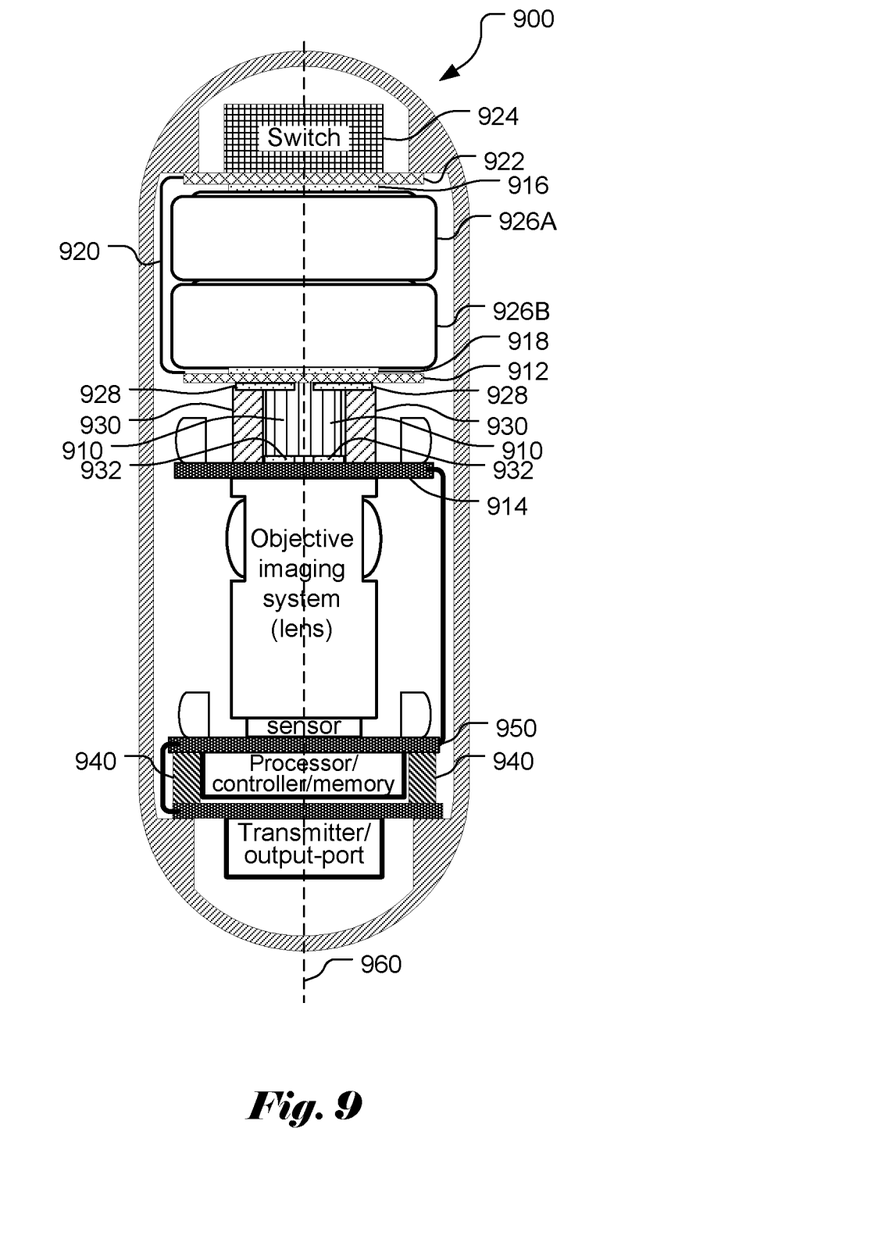
FIG. 9 illustrates a capsule device uses an electrical interconnect with pressure contacts between the power source and the capsule sub-system connecting the second circuit board to the power-output nodes

FIG. 9 shows an exemplary capsule system incorporating an embodiment of the present invention. Capsule system 900 uses flexible compliant electrical interconnect 910 to connect the power source to a capsule subsystem with pressure contacts at one or both sides of the electrical interconnect. Flexible compliant electrical interconnect 910 allows multiple pressure contacts to be made between two circuit boards 912 and 914. The power source comprises batteries 926A and 926B that are coupled to circuit board 912 via battery contact pads 916 and 918, flexible cable 920, and circuit board 922. Furthermore, the connection from the batteries to the circuit board 912 is controlled by switch 924, which incorporates an embodiment of the present invention such as the switch illustrated in FIG. 6. An electrical interconnect with rigid conductors is generally unable to apply adequate pressure for all conductors simultaneously. The electrical interconnect may be intersected by a center line of the capsule so that an excessive moment is not applied to the power source or the capsule subsystem. The electrical interconnect may be an elastomeric connector such as a Zebra connector, pogo pins, springs, flexible metal tabs, or any other device with flexible conductors that maintains an electrical connection between metal contacts on either side of the electrical interconnect. FIG. 9 illustrates an example of using contacts 928 and 932 connected to respective circuit boards 912 and 914 to allow electrical interconnect 910 to connect circuit boards 912 and 914. However, one side of electrical interconnect 910 may have conductors soldered to a PCB while the other side forms pressure contacts. At least one side of the electrical interconnect forms a pressure contacts to a circuit board, either in the power source or in the capsule subsystem. Stop mechanism 930 sits between the power source and the subsystem so that the compression of electrical interconnect 910 is limited. In order to push the sub-system towards the power source until it reaches the stop mechanism 930, spring 940 can be used. In the exemplary system shown in FIG. 9, the spring 940 pushes the circuit board 950 and the force exerted by spring 940 further pushes circuit board 914 towards the power source. The stop mechanism may also serve as a holder to constrain the motion of electrical interconnect 910. The stop mechanism may be attached to the capsules subsystem, the power source, both, or neither. Electrical interconnect 910 can be located along a longitudinal centerline 960 of the capsule.

The above description is presented to enable a person of ordinary skill in the art to practice the present invention as provided in the context of a particular application and its requirement. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the above detailed description, various specific details are illustrated in order to provide a thorough understanding of the present invention. Nevertheless, it will be understood by those skilled in the art that the present invention may be practiced.

The invention claimed is:

1. A power source apparatus for medical capsules, comprising:
   a plunger responsive to a magnetic field;
   a spring disposed to interact with the plunger, wherein the plunger is at a first position to press the spring when the magnetic field is applied and the plunger is pushed by the spring to a second position when the magnetic field is removed;
   one or more batteries comprising a positive terminal and a negative terminal; and
   two power-output nodes coupled to said one or more batteries and the plunger, wherein one of said two power-output nodes is electrically connected to the positive terminal and another of said two power-output nodes is electrically connected to the negative terminal and at least one of said two power-output nodes is connected to the positive terminal or the negative terminal electrically to enable electrical power from said one or more batteries at said two power-output nodes when the plunger is at the second position, and at least one of said two power-output nodes is electrically disconnected to disable the electrical power from said one or more batteries at the power-output nodes when the plunger is at the first position.

2. The power source apparatus of claim 1, wherein the plunger comprises a ferromagnetic material or a ferrimagnetic material.

3. The power source apparatus of claim 1, wherein the spring is disposed to have one side of the spring against a fixed structure and other side of the spring against one side of the plunger and another side of the plunger is facing said one or more batteries.

4. The power source apparatus of claim 1, wherein the spring is a cantilever spring.

5. The power source apparatus of claim 1, wherein the spring is a coil spring.

6. The power source apparatus of claim 1, wherein the plunger comprises a rod-portion and a flange-portion, and wherein the spring is disposed around the rod-portion of the plunger to have one side of the spring against a fixed structure and other side of the spring against the flange-portion.

7. The power source apparatus of claim 1, further comprising a first circuit board having said two power-output nodes disposed on one side of the first circuit board with other side of the first circuit board facing said one or more batteries, wherein said one or more batteries are disposed between the plunger and the first circuit board.

8. The power source apparatus of claim 7, further comprising a second circuit board with one side of the second circuit board attached to the plunger and with other side of the second circuit board facing said one or more batteries, wherein an electrical interconnect connects between a power pad on the second circuit board to one of said two power-output nodes, and wherein the power pad is electrically connected to one of the positive terminal and the negative terminal when the plunger is in the second position, and the power pad is electrically disconnected from said one of the positive terminal and the negative terminal when the plunger is in the first position.

9. The power source apparatus of claim 8, further comprising a switch holder to hold the plunger and the spring, wherein the switch holder, the plunger, the spring, said one or more batteries, the first circuit board, the second circuit board and the electrical interconnect are shrink wrapped using a heat sensitive material into a power switch module.

10. The power source apparatus of claim 7, further comprising a second circuit board arranged to be stationary with one side of the second circuit board contacting one of the positive terminal and the negative terminal electrically and with other side of the second circuit board facing the plunger, wherein a first contact pad and a second contact pad are disposed on said other side of the second circuit board with the first contact pad connected to one of the positive terminal and the negative terminal and with an electrical interconnect connects between the second contact pad to one of said two power-output nodes, and the first contact pad is electrically connected to the second contact pad when the plunger is in the second position, and the first contact pad is electrically disconnected from the second contact pad when the plunger is in the first position.

11. The power source apparatus of claim 10, further comprising a switch holder to hold the plunger and the spring, wherein the switch holder, the plunger, the spring, said one or more batteries, the first circuit board, the second circuit board and the electrical interconnect are shrink wrapped using a heat sensitive material into a power switch module.

12. The power source apparatus of claim 1 further comprising a switch holder to hold the plunger and the spring, wherein the switch holder, the plunger, the spring and said one or more batteries are shrink wrapped using a heat sensitive material into a power switch module.

13. The power source apparatus of claim 12, wherein the switch holder surrounds the plunger, and the spring to constrain lateral motion of the plunger and the spring.

14. The power source apparatus of claim 12, wherein the switch holder, the plunger, the spring and said one or more batteries are stacked vertically to form vertically stacked parts, and wherein the heat sensitive material is applied around said vertically stacked parts.

15. The power source apparatus of claim 1, wherein the magnetic field is caused by a magnet near the plunger.

16. A capsule camera system, comprising:
a housing adapted to be swallowed;
a power source within the housing comprising:
    a plunger responsive to a magnetic field;
    a spring disposed to interact with the plunger, wherein the plunger is at a first position to press the spring when the magnetic field is applied and the plunger is pushed by the spring to a second position when the magnetic field is removed;
    one or more batteries comprising a positive terminal and a negative terminal; and
    two power-output nodes coupled to said one or more batteries and the plunger, wherein one of said two power-output nodes is electrically connected to the positive terminal and another of said two power-output nodes is electrically connected to the negative terminal and at least one of said two power-output nodes is connected to the positive terminal or the negative terminal electrically through the plunger to enable electrical power from said one or more batteries at said two power-output nodes when the plunger is at the second position, and at least one of said two power-output nodes is electrically disconnected to disable the electrical power from said one or more batteries at the power-output nodes when the plunger is at the first position; and
a capsule sub-system within the housing comprising:
    a light source;
    a camera for capturing a digital image of a scene illuminated by the light source; and
    an archival memory to store data and/or a transmitter to transmit the data, wherein the data corresponds to the digital image; and
wherein the capsule sub-system is coupled to said two power-output nodes to receive power from the power source.

17. The capsule camera system of claim 16, wherein the housing has an elongated shape, and wherein the power source and the capsule sub-system are stack longitudinally inside the housing.

18. The capsule camera system of claim 17, wherein the magnetic field is caused by a magnet placed near one end of the housing close to the power source.

* * * * *